Figure 1:
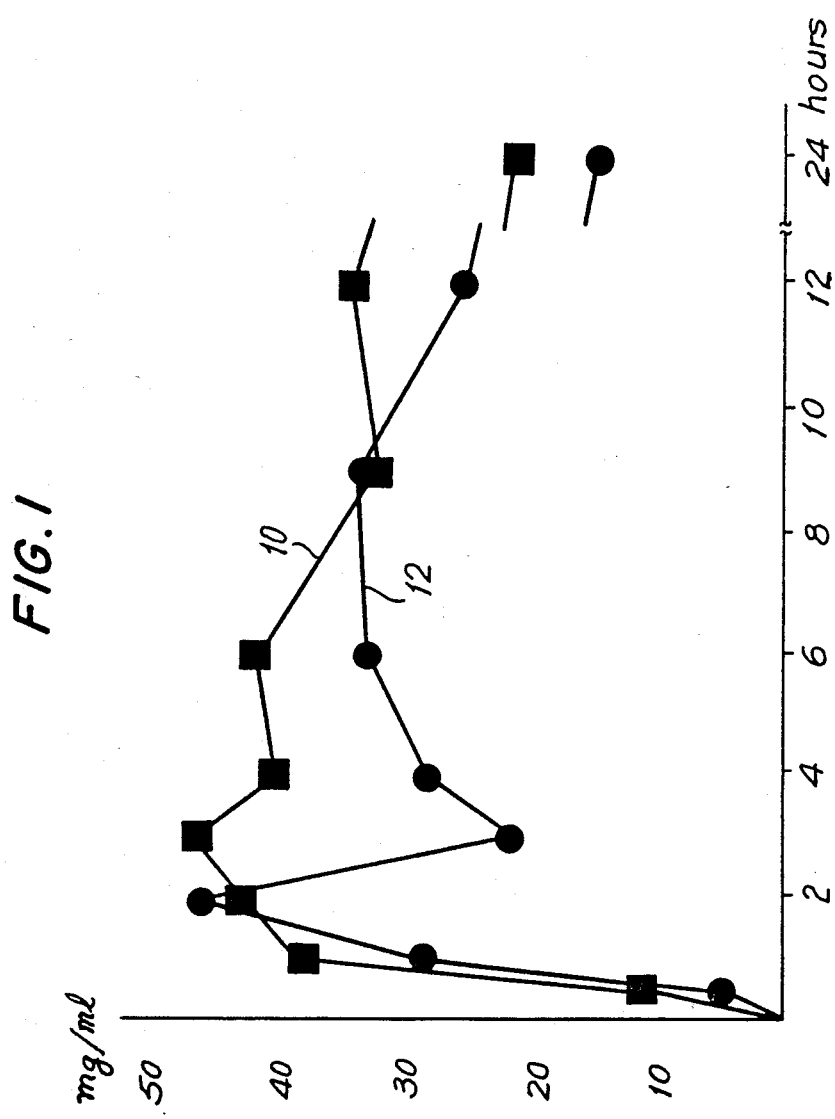

United States Patent [19]
Lowey

[11] Patent Number: 4,855,143
[45] Date of Patent: Aug. 8, 1989

[54] METHOD OF PREPARING CONTROLLED LONG-ACTING PHARMACEUTICAL FORMULATIONS IN UNIT DOSAGE FORM HAVING UNIFORM AND COMPARABLE BIOAVAILABILITY CHARACTERISTICS

[76] Inventor: Hans Lowey, 1045 Nine Acres La., Mamaroneck, N.Y. 10541

[21] Appl. No.: 218,697

[22] Filed: Jul. 12, 1988

Related U.S. Application Data

[62] Division of Ser. No. 848,702, Apr. 4, 1986, Pat. No. 4,775,535.

[51] Int. Cl.$^4$ .......................... A61K 9/22; A61K 9/26
[52] U.S. Cl. ..................................... 424/468; 424/469; 424/470; 424/488; 424/494
[58] Field of Search ............... 424/468, 469, 470, 488, 424/494

[56] References Cited

U.S. PATENT DOCUMENTS

| | | | |
|---|---|---|---|
| 2,980,589 | 4/1961 | DeGrunigen | 167/82 |
| 3,065,143 | 11/1962 | Christenson et al. | 424/35 |
| 3,079,303 | 2/1963 | Raff et al. | 167/82 |
| 3,758,679 | 9/1973 | Seidler | 424/19 |
| 3,852,421 | 12/1974 | Koyanagi et al. | 424/189 |
| 3,870,790 | 3/1975 | Lowey | 424/19 |
| 3,957,525 | 5/1976 | Ohno et al. | 106/189 |
| 4,226,849 | 10/1980 | Schor | 424/19 |
| 4,235,870 | 11/1980 | Leslie | 424/19 |
| 4,259,314 | 3/1981 | Lowey | 424/19 |
| 4,357,469 | 11/1982 | Schor | 424/19 |
| 4,369,172 | 1/1983 | Schor et al. | 424/19 |
| 4,389,393 | 6/1983 | Schor et al. | 424/19 |
| 4,540,566 | 9/1985 | Davis et al. | 424/19 |

FOREIGN PATENT DOCUMENTS

| | | |
|---|---|---|
| 945899 | 4/1974 | Canada . |
| 1070492 | 1/1967 | United Kingdom . |
| 1171691 | 11/1969 | United Kingdom . |
| 1279214 | 6/1972 | United Kingdom . |
| 1430684 | 3/1976 | United Kingdom . |
| 1583801 | 2/1981 | United Kingdom . |

*Primary Examiner*—Shep K. Rose
*Attorney, Agent, or Firm*—Curtis, Morris & Safford

[57] ABSTRACT

A method of preparing a multiplicity of controlled, long-acting release pharmaceutical tablets, each containing a therapeutic agent and a cellulosic ether carrier base material is shown. The method includes the steps of adding a quantity of cellulose ether base material such as hydroxypropyl methylcellulose and an active therapeutic agent to form a mixture, thoroughly and uniformly mixing that mixture, discontinuing the mixing, permitting the uniform mixture to stand for a period of time, typically two to twenty-four hours or longer, sufficient to cause the therapeutic agent to become bonded to the carrier base material and compressing portions of the mixture to form the solid unit dose tablets. The advantage of the method is that the time release of each tablet from a given batch of formulation and the time release characteristics of tablets prepared in different batches, will be substantially more uniform and comparable.

12 Claims, 7 Drawing Sheets

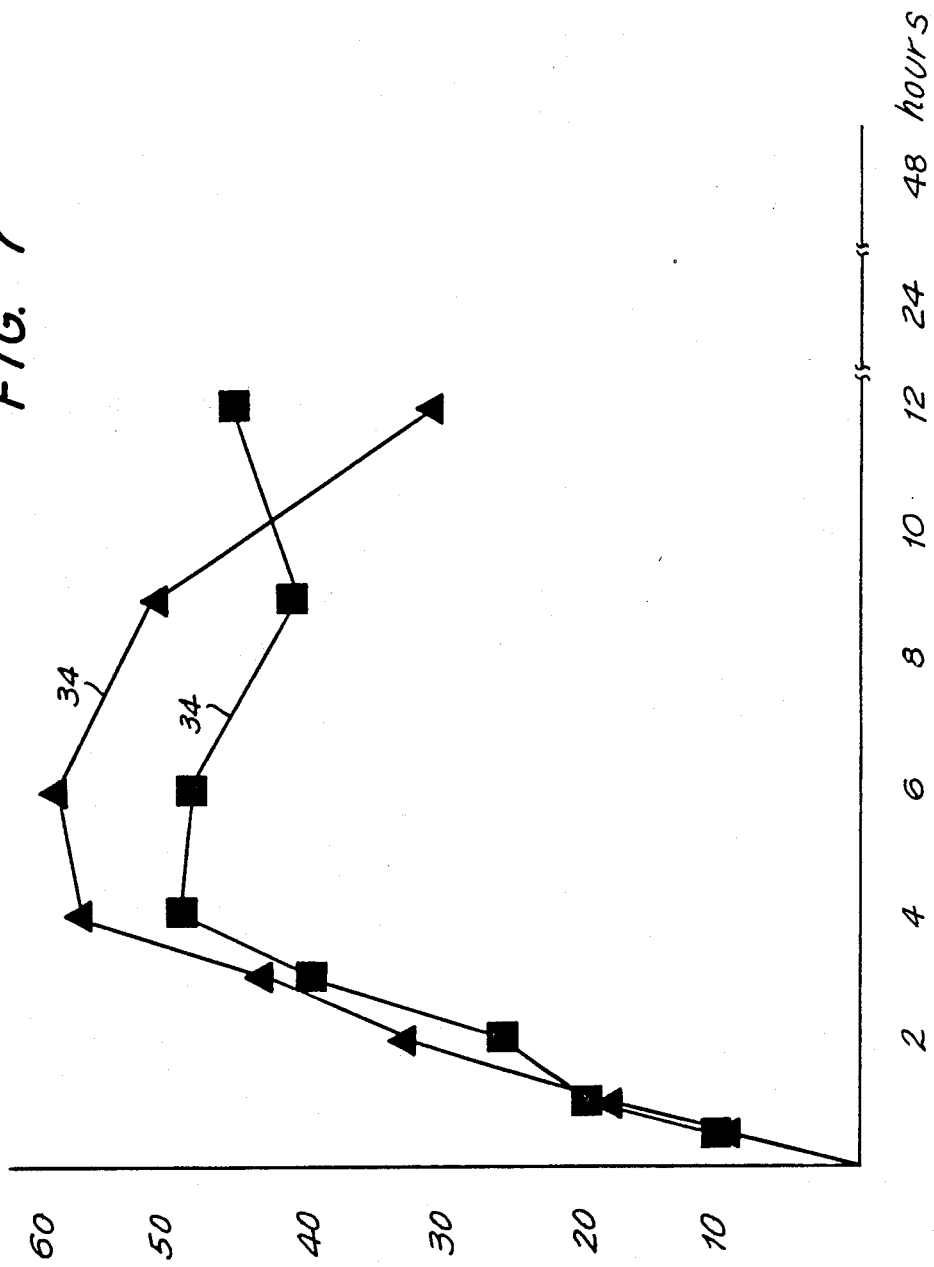

METHOD OF PREPARING CONTROLLED LONG-ACTING PHARMACEUTICAL FORMULATIONS IN UNIT DOSAGE FORM HAVING UNIFORM AND COMPARABLE BIOAVAILABILITY CHARACTERISTICS

This application is a division of application Ser. No. 848,702, filed Apr. 4, 1986, now U.S. Pat. No. 4,775,535.

BACKGROUND OF THE INVENTION

I. Field of The Invention

This invention relates to a method of preparing a controlled long-acting release pharmaceutical formulation containing an active therapeutic agent and a carrier base material in unit dosage form. More specifically, this invention relates to a method of preparing batches of unit doses of oral tablets, lozenges, suppositories and the like, of a controlled long-acting pharmaceutical formulation containing an active therapeutic agent and a carrier base material, wherein each of the unit doses has a substantially comparable and uniform bioavailability characteristic when consumed. The invention also relates to the improved unit dosage forms prepared by the method of the invention.

This invention relates broadly to controlled long-acting pharmaceutical formulations containing a variety of active therapeutic agents and carrier base materials consisting of at least one cellulose ether. The cellulose ethers typically used in the methods and compositions of the invention are hydroxyalkyl celluloses or hydroxyalkyl alkylcellulose materials such as hydroxypropyl methylcellulose and similar analogs.

Long-acting products are widely marketed in the pharmaceutical field and are now a significant factor in the administration of a variety of active pharmaceutical agents. The advantages of such long-acting or sustained release products are now well understood and a very substantial industry has developed around these products. Sustained release products permit various medications to be administered for uniform and continuous release over a prolonged period of time thereby achieving a particular blood level of active ingredient for whatever time is thought to be advantageous to the patient. Such administration obviates the necessity for requiring frequent administration of active ingredient and avoids the problems inherent in insuring timely and repetitive consumption of pharmaceutical product by the patient. It is possible to achieve stable blood levels of a variety of active therapeutic agents and thereby control a variety of physiological conditions. It also reduces or possibly eliminates toxic or side effects which are caused by frequent administration of active ingredients through the peaks and valleys of blood levels caused by multiple ingestion of medication.

II. Description of The Prior Art

The use of cellulosic derivatives, more particularly cellulose ethers such as hydroxypropyl methylcellulose as a carrier in long-acting or sustained release pharmaceutical formulations is well known. A variety of commercial forms of cellulosic ethers are commercially available and these include methylcellulose, hydroxypropyl methylcellulose, ethyl cellulose, carboxymethyl cellulose and hydroxypropyl cellulose, and derivatives, among others. These cellulose ethers are each available in a range of molecular weights and viscosities and under a variety of trade names.

Hydroxypropyl methylcellulose is a particularly preferred cellulose ether for the sustained release compositions of the invention and it is available from Dow Chemical Company under the Methocel trademark. The several hydroxypropyl methylcellulose products have varying methoxyl and hydroxypropoxyl contents as well as different molecular weights. Typically, the methoxyl content ranges from 16.5 to 30 weight percent and the hydroxypropyl content ranges from 4 to 32 weight percent. The viscosities of the several grades of hydroxypropyl methylcellulose, as calculated based on the viscosity of a 2% aqueous solution at 20° C., range from 5 cps to 100,000 cps. Typically the higher viscosity grade materials dissolve more slowly and can be used in lesser amounts than comparable materials having lesser viscosities.

The prior art dates back to about the 1960's. Christiansen et. al., U.S. Pat. No. 3,065,143, disclosed the use of hydroxypropyl methylcellulose in sustained release tablets. Lowey et al., in U.S. Pat. No. 3,870,790, disclosed processes for mixing an active therapeutic ingredient with premoisturized hydroxypropyl methylcellulose which could also optionally be mixed with ethylcellulose. The sustained release properties of the resulting mixture could be controlled by the moisture content of the carrier material which was in turn set in a moisturizing process wherein the carrier material was subjected to elevated temperature and humidity conditions.

Lowey, U.S. Pat. No. 4,259,314, disclosed sustained release products which consisted of mixtures of hydroxypropyl methylcellulose having a viscosity of from 50 to 4,000 cps and hydroxypropyl cellulose. These mixtures, particularly when dried to less than one percent moisture, were advantageously used with hygroscopic active agents.

Other workers, including Schor et al., U.S. Pat. No. 4,389,393, have disclosed sustained release compositions wherein the carrier base material is selected from certain preferred forms of hydroxypropyl methylcellulose having certain defined viscosities, methoxyl contents, hydroxypropyl contents and number average molecular weights.

In preparing tablets according to prior art methods, the carrier base material is first prepared. A mixture of cellulosic components can be employed and, if deemed desirable, the carrier base mixture can be treated by humidification or other process steps. The active ingredient is then added to the carrier base material and thoroughly intermixed with the base to form a uniform mixture. The mixture of active ingredient and carrier is removed to the hopper of a tableting machine. Such machines are well known in the art and may have variable size punches preset and are adjustable to control the compression of the tablet. For example, punches and dies from 5/32 to ¾ inches can be employed and the tableting machines may be adjusted to vary the compressive pressure from 6 to 14 kg/cm$^2$. These variables and the control of them are well understood in the prior art and it is recognized that sustained release properties are a function both of the size of the tablet and the compression to which it is subjected. Thus ¼ to 15 grain tablets can be produced according to prior art methods.

It is of considerable importance in the administration of controlled, long-acting release pharmaceutical tablets, lozenges and the like, that the rate of release of the active agent from the tablet be consistent and uniform among tablets prepared in a given manufacturing batch and among tablets prepared at different times in different manufacturing batches. It is critical, both from the standpoint of the safety of the administration of the therapeutic agent as well as the reliability thereof, that the bioavailability characteristic of the tablets prepared be substantially uniform and comparable. In the absence of such reliability, the dangers to a patient are significant because active ingredient may be release at faster or slower rates than are assumed. For example, where nitroglycerin is being administered to angina patients via oral or buccal tablets, such variation in release may be life-threatening. The problem of noncomparable release rates among presumably identical tablets is particularly exacerbated where those tablets are of the "one-a-day" type and where the patient is relying upon a uniform and comparable release day after day from these tablets.

A problem that has confronted the art is that of preparing multiple long-acting tablets wherein each tablet releases the active ingredient uniformly and comparably. To achieve the proper bioavailability of active ingredient over time from tablet to tablet and from batch to batch requires not only that the same amount of active ingredient be incorporated within each tablet but that the active ingredient be thoroughly mixed and bonded to the cellulosic carrier base material in the same manner so that release is not faster from one tablet than from another.

SUMMARY OF THE INVENTION

It is a primary object of this invention to provide a method for preparing controlled long-acting pharmaceutical formulations containing active therapeutic agent and carrier base material, in unit dosage form, as an oral tablet which insures that the unit dosage form, has uniform and comparable bioavailability characteristics.

Another object of this invention is to provide a method for preparing a multiplicity of unit doses of a controlled, long-acting release pharmaceutical formulation which unit doses are safer and more reliable to administer to patients.

It is still a further object of this invention to prepare unit dosage forms of sustained action pharmaceutical formulations which have the advantage of greater uniformity of bioavailability.

These and other objects of the invention are achieved in a method wherein a carrier base material comprising at least one cellulose ether is thoroughly mixed with an active therapeutic agent to form a substantially uniform pharmaceutical formulation, the mixing is thereafter discontinued, the so-formed mixture is permitted to stand for a period of time sufficient to cause the therapeutic agent to become bonded to the cellulose ether (a step referred to herein as tempering) and the so-tempered pharmaceutical formulation is shaped and compressed into a suitable unit dosage form.

The objects of the invention are achieved where a quantity of solid carrier base material consisting essentially of one or more cellulose ethers selected from the group consisting of hydroxypropyl methylcellulose, hydroxypropyl cellulose, carboxymethyl cellulose and ethyl cellulose or derivatives are intermixed with a therapeutically active pharmaceutical agent in granular or powder form, the mixture is mechanically stirred until the agent and the base material are uniform, the mixing step is discontinued and the uniform mixture is permitted to reside for a period of time, typically two to twenty-four hours or longer, sufficient to cause the granules of therapeutic agent to become bonded by a physical and/or physical-chemical adherence to the particles of carrier base material, and, wherein the so-tempered mixture is shaped and compressed into a solid unit dosage form as an oral tablet.

The unit dosage forms prepared by the methods of the invention are characterized by uniform and comparable time release characteristics, i.e., the active ingredient is released at comparable rates by each of a multiplicity of tablets formed from a given batch of mixed carrier material and therapeutic agent. In contrast to prior art compositions which are not tempered according to the invention, the tablet time release characteristic is substantially more uniform and batch to batch variations in time release characteristics are likewise substantially reduced.

To achieve uniform and comparable time release of active ingredient or, as stated otherwise, to achieve a uniform and comparable bioavailability characteristic for each unit dose prepared from a batch of carrier material and active ingredient, requires (1) that the same amount of active ingredient be present per unit of base material in each unit dosage form and that the active be thoroughly mixed with the base, and, (2) that the thoroughly intermixed active ingredient and carrier base material be permitted to reside, in the absence of mixing, for a time sufficient to permit tempering to occur, i.e., a time sufficient to permit the active ingredient to bond to the carrier material by a process of physical adherence or chemical-physical adherence.

Whether the base includes one cellulose ether or a mixture of cellulose ethers or one or more cellulose ethers having differing viscosity characteristics, the mixture of that base and the particular active ingredient should not be tableted immediately after mixing the base and the active ingredient. Following that prior art technique, there is no satisfactory reproducibility, from tablet to tablet, or from batch to batch, of the time release characteristic of the unit dosage forms which are produced. This results in very significant differences in the hourly release times of tablets made from different batches of the same carrier/active ingredients and results in substantial differences in hourly release times of the active ingredient from tablet to tablet from a given batch of base and active ingredient. This is obviously unsatisfactory from a medicinal administration standpoint and may result to significant medical problems.

It is thought that failure to permit the carrier/active-ingredient mixture to temper may result in a separation of the active ingredient from the base material as the mixture is handled during the shaping and compressing steps which follow the mixing in the prior art. In this regard, it is observed that the manufacture of controlled release tablets cannot be properly compared with the manufacture of regular oral pharmaceutical tablets. In the latter case, the important factor is to release the active ingredient as quickly as possible, whereas uniform and comparable release characteristics are sought with controlled action formulations.

The exact nature of the bond between the granules of active ingredient and the granules of cellulose ether cannot be precisely characterized. It is understood in the art, however, that methyl cellulose and other cellulosic ethers are useful in adhesives, that they are thermoplastic in nature, that they have thermogelling properties, and that they can bind themselves into self binding tablets. Accordingly, without adopting any particular theory, it is believed to be central to the instant invention to permit the active ingredient and the carrier base material to stand, undisturbed, for a time sufficient to permit the polymeric base material and the active material to bond by whatever physical or physical-chemical process controls. It is also believed that the bonding reactions which take place are equilibrium reactions and that accordingly the benefits of this invention are achieved after a tempering period sufficient to permit the bonding action to approach the equilibrium.

The efficacy of the bond between the granular active ingredient and the particles of the carrier base material is also believed to be affected by the sizes of the particles themselves and by their configuration. Thus, controlling the particle size of the active agent and the base material, or their respective particle configurations, so as to create a lock-and-key interaction may be of substantial benefit in the tempering process and may reduce the amount of time necessary to reach a desired equilibrium.

It may be possible, to some degree, to control the time release characteristic of formulations containing carrier base material and active therapeutic agent by varying the length of time that the mixture is tempered. That is, where a large initial release is necessary to reach a therapeutic level as soon as possible, it may be desirable to shorten the length of the tempering step. in contrast, where a steady and constant release rate is desirable over a longer period of time, it may be useful to lengthen the tempering step and enhance the bonding of the active ingredient to the carrier base material.

In sustained action drug administration, it is some times desirable to have a relatively rapid release of active ingredient up to a certain blood level concentration and then to maintain either constant or slightly declining blood level concentration. These objects are achieved with the invention, whereas in the prior art, as will be demonstrated in the comparative examples below, wide variations may occur in the bioavailability of the active ingredient where the inventive method is not employed.

It will be recognized by those skilled in the art that the method of the invention goes a full step beyond the techniques taught in the United States Pharmacopoeia for controlling dosage-form uniformity in compressed tablets. The United States Pharmacopoeia - NF, Second Supplement, describes weight variation and content uniformity tests for tablets. For compressed tablets (coated or uncoated), the prescribed tests require weight variation or content uniformity testing of multiple dosage units and a statistical analysis of those results to determine whether the multiple tablets within a given batch are sufficiently uniform in their content of active ingredient. The following test is quoted from U.S.P. - NF, Second Supplement, Physical Tests/Uniformity of Dosage Units, page 905.

(A) If the average of the limits specified in the potency definition in the individual monograph is 100.0 percent or less--
COMPRESSED TABLETS (COATED OR UNCOATED), SUSPENSIONS IN SINGLE UNIT CONTAINERS, SOLIDS (INCLUDING STERILE SOLIDS) IN SINGLE UNIT CONTAINERS, and STERILE SOLIDS FOR PARENTERAL USE. Unless otherwise specified in the individual monograph, the requirements for dose uniformity are met if the amount of the active ingredient in each of the 10 dosage units as determined from the Weight variation of the Content uniformity method lies within the range of 85.0 percent to 115.0 percent of the tablet claim and the Relative standard deviation is less that or equal to 6.0 percent.

If 1 unit is outside the range of 85.0 percent to 115.0 percent of label claim and no unit is outside the range of 75.0 percent to 125.0 percent of label claim, or if the Relative standard deviation is greater than 6.0 percent, or if both conditions prevail, test 20 additional units. The requirements are met if not more than 1 unit of the 30 is outside the range of 85.0 percent to 115.0 percent of label claim and no unit is outside the range of 75.0 percent to 125.0 percent of the label claim and the Relative standard deviation of the 30 dosage units does not exceed 7.8 percent The foregoing tests, whether based on weight variation or content uniformity, are not ultimately suitable for proper reliability testing of unit-dosage forms from a batch of intended time release formulation. That is because even with a satisfactory statistical performance with respect to weight variation and content uniformity, the time release characteristics of active ingredient from such tablets may vary markedly because the active ingredient has not been permitted to bond to the carrier material according to the instant invention.

The invention is not limited to the use of any particular cellulose ethers, and those skilled in the art will recognize that a single cellulose ether or mixture of ethers can be used as can a variety of viscosity grades of the several commercially available cellulose ethers. Broadly, it is preferred to use hydroxyalkyl cellulose and/or hydroxyalkyl alkylcellulose such as hydroxypropyl methylcellulose, hydroxypropyl cellulose, hydroxyethyl cellulose, carboxymethyl cellulose and other similar compounds or derivatives. Preferred among these are hydroxypropyl methylcellulose and hydroxypropyl cellulose, the former being obtainable in a variety of viscosity grades from 3 cps to 100,000 cps from Dow Chemical Company under its trade name Methocel and the latter being available from Hercules, Inc., under its trademark Klucel. Advantageous carrier bases can be prepared using Methocel E50 (50 cps), Methocel E4M (4,000 cps), and Methocel K15M (15,000 cps).

The active ingredients combined with the carrier base material can be of any type which acts systemically or locally. Those which act systemically are typically administered orally, the object being to deliver reliable and constant amounts of active agent into the blood stream. Those types of active ingredients which act locally may be employed in buccal tablets or in vaginal or rectal suppositories.

Among the active therapeutic agents which can be combined with carrier base material according to the method of the invention are sedatives, vitamins, anti-inflammatory agents, vasodilators, stimulants, relaxants, suppressants, and many other types of therapeutic agents.

Among the active ingredients which can be used in the method of the invention are, for example, isosorbide dinitrate or mononitrate (employed in the treatment of angina pectoris), theophylline (employed in the treatment of asthma), nitroglycerin, ibuprofen, and acetaminophen.

In preparing the pharmaceutical compositions of the invention, the desired ratio of active ingredient and a carrier base material is introduced into a mixing vessel. Other ingredients to be included in the final unit dosage form may be introduced into the mixing vessel, for example, fillers, drying agents, lubricants, coloring agents, starch, and other materials well known in the art. Thereafter the base mixture is typically agitated and mixed for from 20 to 40 minutes and usually from 30 to 40 minutes to achieve uniformity of the active ingredients with the base mixture. Mixing equipment may be, for example, a Day mixer or a Pony mixer.

the tempering step which is critical to the instant invention is usually carried out in the same or a different vessel from that in which the mixing has taken place. The uniformly mixed material is permitted to stand, substantially undisturbed for a period of 2 to 72 hours, preferably 4 to 48 hours, while the active ingredient bonds to the plastic carrier base material.

After the uniform mixture has been tempered for a sufficient time to cause the bonding to take place, it is transferred to a shaping and compressing step as is well known in the art. The equipment used for such steps may be, for example, Stokes or Colton rotary machines or other tablet compressing machines. Typical compression used in the shaping and compressing step varies from 6 to 12 kg/cm$^2$ and preferably is in the range of 8 to 12 kg/cm$^2$. The unit dosage forms prepared in this final step are oral tablets.

The invention is further described in the following examples and in the drawings.

EXAMPLES

A series of sustained release oral tablets were prepared by the method of the invention and by the prior art method and their respective sustained release performance was tested.

EXAMPLE I-IV

Method of Oral Tablet Preparation

The base ingredients listed below were mixed for about 20 minutes in a Day powder mixer or a Pony mixer. Active ingredient was added to the base mixture and the mixture was again mixed for about 30 minutes adding lubricants. Finally the complete mixture was permitted to temper for bonding for not less than 24 hours at room temperature. The tablets were compressed into scored capsule-shaped oral tablets. The punch size was 19 mm $\times$ 8.5 mm and the hardness was 9 kg/cm$^2$. In each instance, the potency of the tablet was 120 mg.

Release of Active Ingredient

The release of active ingredient from the tablets prepared in Examples I-IV was determined by blood level tests performed, in each instance, on six volunteers. The volunteers were all healthy adults. Each volunteer underwent a careful medical examination before the first treatment, including measurement of arterial blood pressure and pulse rate, blood cell count, blood glucose, urea, creatinine, bilirubin and a complete urinalysis. The mean age of the volunteers was about 36 years and the average body weight was about 70 kilograms. All doses were administered after fasting conditions by the oral administration and ingestion of the tablets with 100 ml of tap water. The mean value of the blood level of active ingredient at the indicated time intervals is shown in FIGS. 1-4.

The release of active ingredient over time from the tablets prepared as described above can also be determined by an in vitro assay which analyzes the percent of the drug released by a single tablet at six time intervals by means of the dissolution test "paddle" apparatus (U.S.P. XX, page 959). In this test, one tablet is placed in a vessel containing 500 ml of pH 1.2 buffer (simulated gastric fluid without enzymes, U.S.P. XX, page 1105) and kept under 125 RPM rotation at 37° C. during the test. At the first, fourth, and eighth hours, the absorbence of the solution is determined at about 278 nm against a pH of 1.2. The following oral tablets were prepared:

| Example I: | |
|---|---|
| Active ingredient X | 120 gm |
| Hydroxypropyl methylcellulose | |
| HPMC E-50 (Dow) | 10 " |
| HPMC E-4M (Dow) | 50 " |
| Hydroxypropyl cellulose | |
| HPC (Hercules) | 10 " |
| Stearic Acid | 1 " |
| Syloid | 2 " |
| Example II: | |
| Active ingredient X | 120 gm |
| HPMC E-50 | 30 " |
| HPMC E-4M | 30 " |
| HPC | 10 " |
| Stearic Acid | 1 " |
| Syloid | 2 " |
| Example III: | |
| Active ingredient | 120 gm |
| HPMC E-50 | 40 " |
| HPMC E-4M | 20 " |
| HPC | 10 " |
| Stearic Acid | 1 " |
| Syloid | 2 " |
| Example IV: | |
| Active ingredient X | 120 gm |
| HPMC E-50 | 10 " |
| HPMC E-4M | 50 " |
| HPC | 10 " |
| Stearic Acid | 1 " |
| Syloid | 2 " |

COMPARATIVE EXAMPLES I-A–IV-A

Oral tablets were prepared according to the prior art method using the same mixtures as are described in Examples I-IV. The tablets of Examples IA-IVA were prepared by mixing the base ingredients listed above for about twenty minutes in a Day powder mixer or pony mixer, adding active ingredient to the base mix and then mixing same again for about thirty minutes while adding lubricants. Then, the mixture was tableted immediately without permitting it to stand or become bonded according to the invention. As in Examples I-IV, the tablets were compressed into scored capsule-shaped tablets using a punch size of 19 mm $\times$ 8.5 mm and a hardness of 9 kg/cm$^2$. Release of active ingredient was determined as described in Examples I-IV.

Comparison of Oral Tablets of The Invention With Oral Tablets of The Prior Art FIG. 1 shows curves of the amount of active ingredient released from the tablet of Example I, reference numeral 10, and from the tablet of Example I-A, reference numeral 12, respectively. It is apparent that the comparative tablet, tablet I-A, which was prepared from a batch not permitted to bond, shows a sharp drop in active ingredient level at about three hours. Moreover, the amount of active ingredient available after twelve hours is substantially lower than in the tablet prepared according to the invention which was permitted to bond for at least twenty-four hours. Moreover, the active ingredient released from the tablet prepared according to the invention had a substantially even release characteristic after reaching its highest active ingredient level at about two hours.

Figure 2:
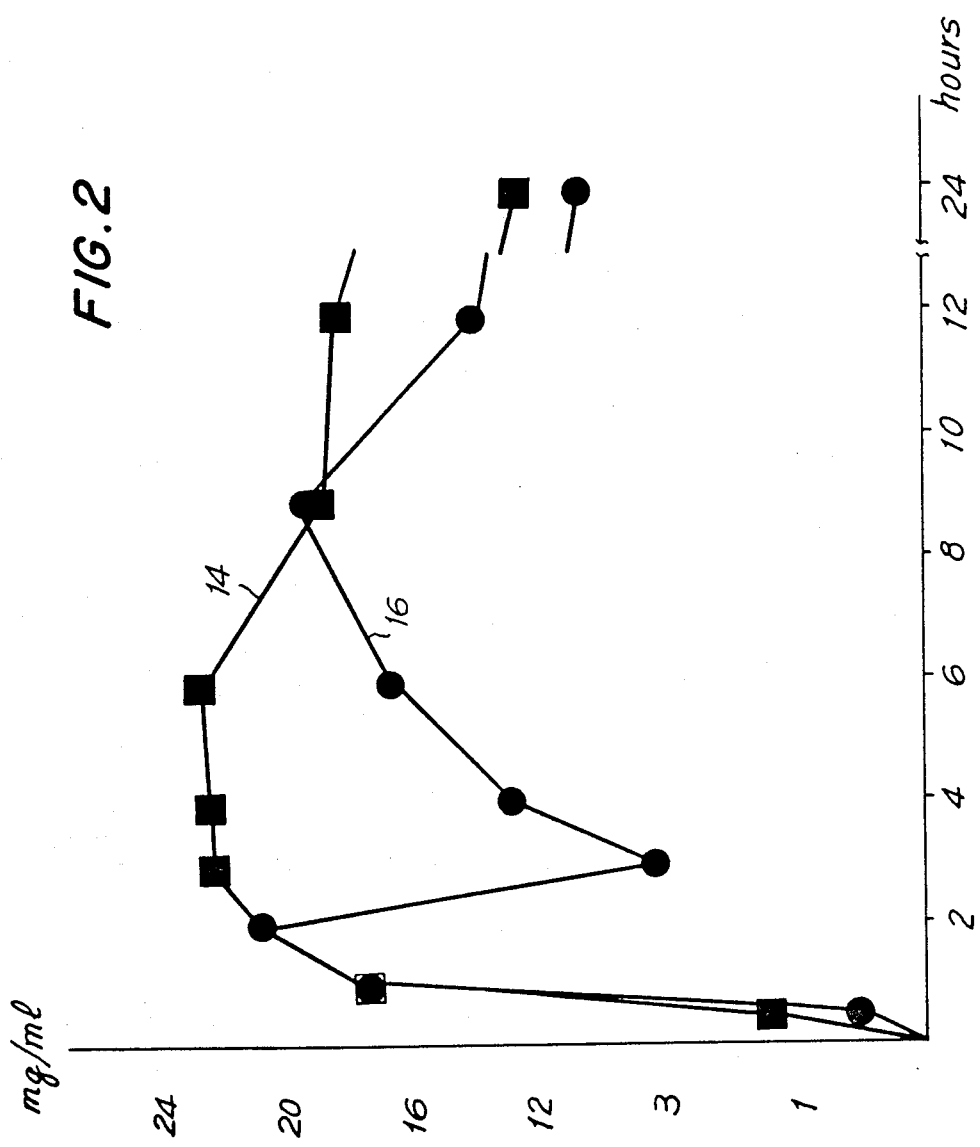

FIG. 2 shows curves of the amount of active ingredient released from the tablet of Example II, 14, and from the tablet of Example II-A, 16, respectively. The release of active ingredient depicted in FIG. 2 substantially confirms the superiority of the bonded tablet. There is an extremely sharp drop in active level at about three hours from the tablet prepared according to the prior art (Example II-A).

Figure 3:
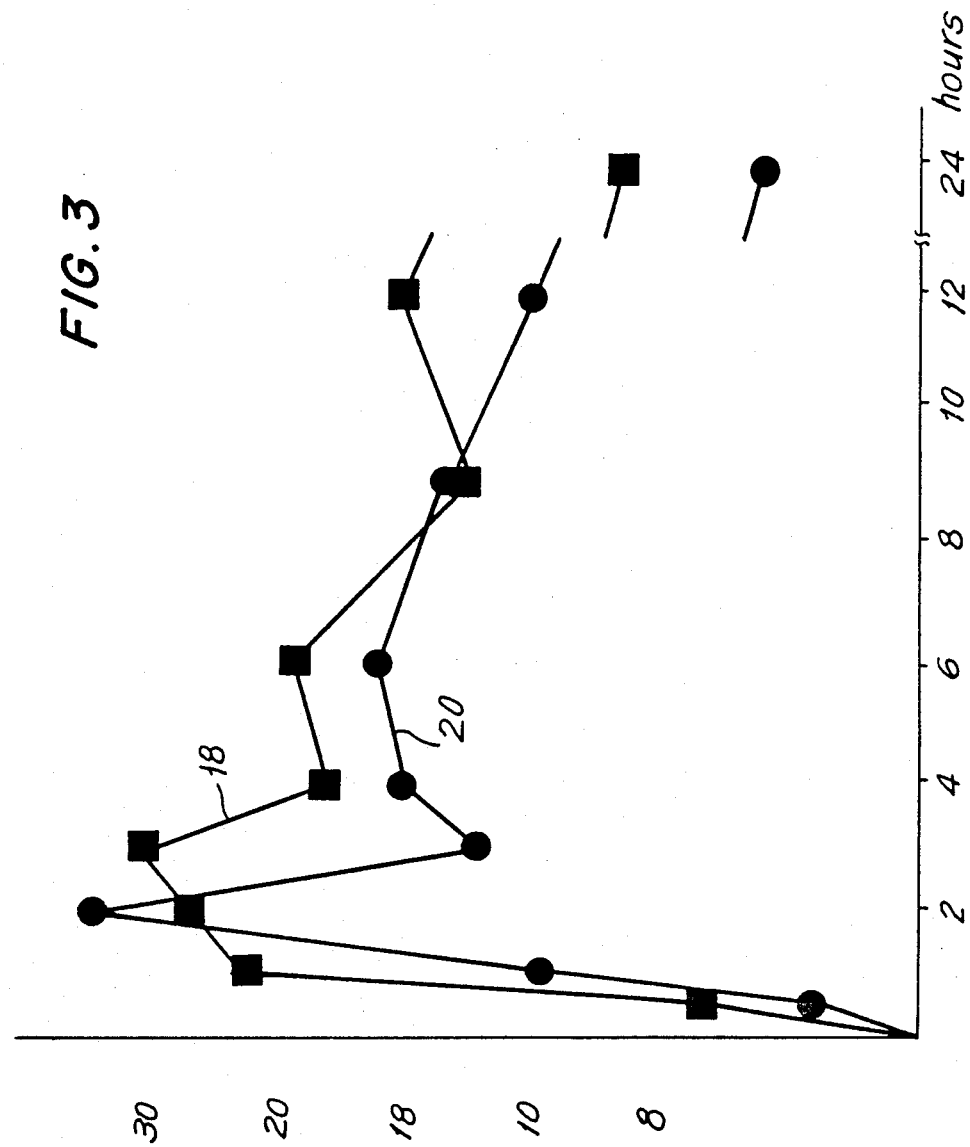

FIG. 3 shows curves of the amount of active ingredient released from the tablet of Example III, 18, and from the tablet of Example III-A, 20, respectively. The results again confirm the superiority of the tablets prepared according to the invention. The drop in active level from comparative tablet III-A was extremely sharp in the third hour.

Figure 4:
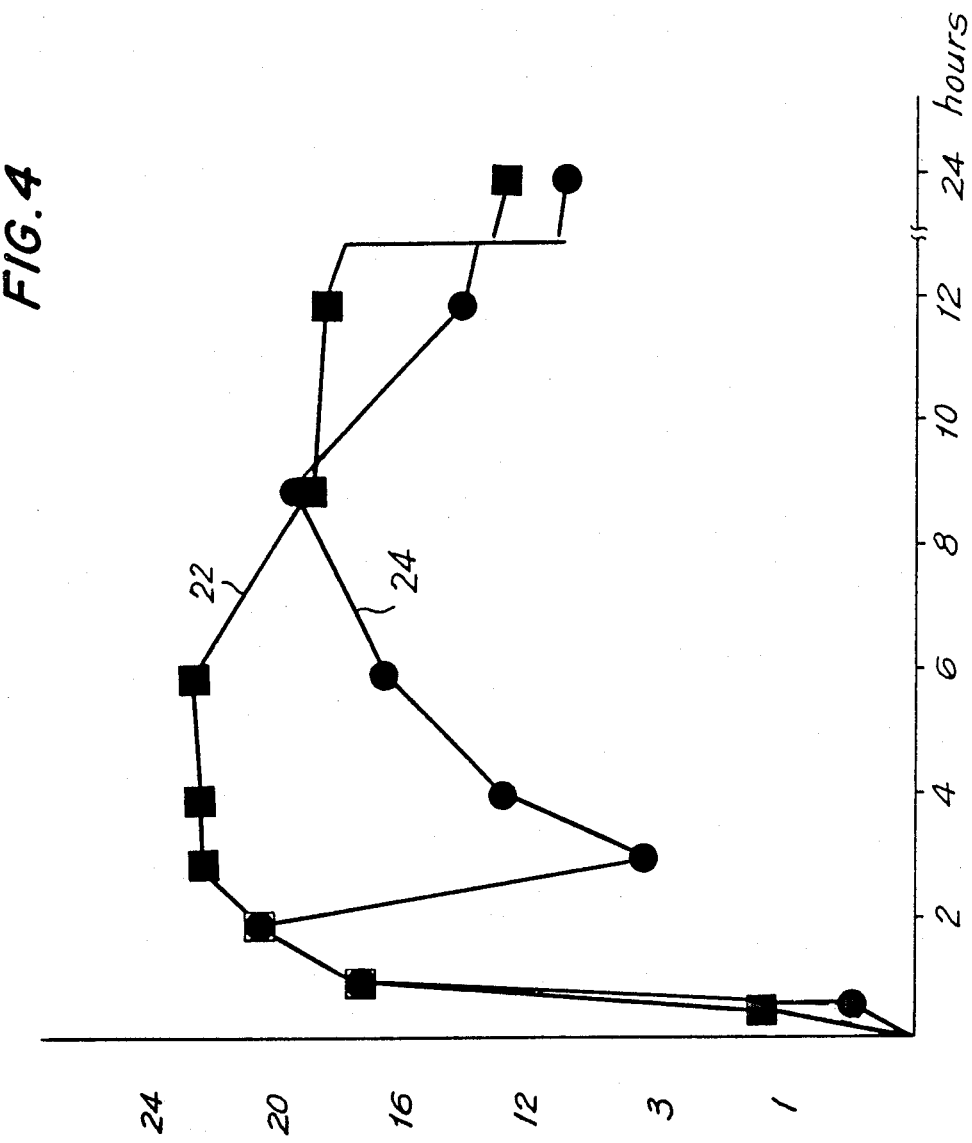

FIG. 4 shows curves of the amount of active ingredient released from the tablet of Example IV, 22, and from the tablet of Example IV-A, 24, respectively. The superiority of the tablet of the invention is confirmed, there being an extremely sharp drop in active level from the unbonded tablet (IV-A) at about the third hour.

EXAMPLE V

Method of Tablet Preparation

The base ingredients listed below are mixed for about 20 minutes in a Day powder mixer or a Pony mixer. Active ingredient was added to the base mixture and the mixture was again mixed for about 30 minutes adding lubricants. Finally the complete mixture was permitted to temper for bonding for not less than 24 hours at room temperature. The tablets were compressed into scored capsule-shaped oral tablets. The punch size was 19.1 mm×9.7 mm and the hardness was 9 kg/cm$^2$. In each instance, the potency of the tablet was 85 mg.

Release of Active Ingredient

Figure 5:
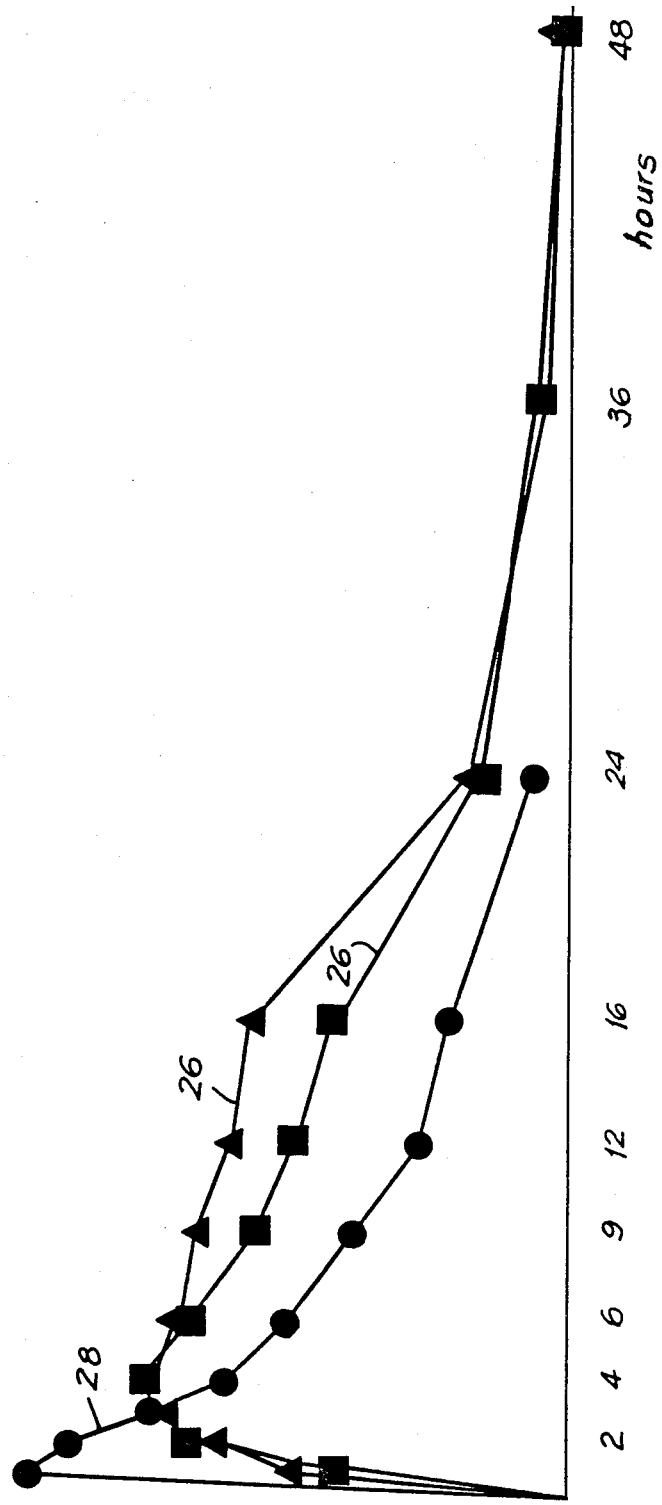

The release of active ingredient from the tablets prepared in Example V was determined by blood level tests performed, in each instance, on six volunteers. The volunteers were all healthy adults. Each volunteer underwent a careful medical examination before the first treatment, including measurement of arterial blood pressure and pulse rate, blood cell count, blood glucose, urea, creatinine, bilirubin and a complete urinalysis. The mean age of the volunteers was about 36 years and the average body weight was about 70 kilograms. All doses were administered after fasting conditions by the oral administration and ingestion of the tablets with 100 ml of tap water. The mean value of the blood level of active ingredient at the indicated time intervals is shown in FIG. 5. Venous blood samples were obtained from each subject just prior to and at 0.25, 0.5, 0.75, 1.00. 1.5, 2.0, 2.5, 3.0, 4.0, 6.0, 9.0, 12.0, 24.0, 36.0 and 48.0 hour times after dosing. In all six (6) subjects, arterial blood pressure was also measured just prior to dosing, and at 1.0, 2.0, 4.0, 6.0 and 9.0 hours after dosing.

The release of active ingredient over time can also be determined by an in vitro assay. This assay determines the percent of the drug released by a single tablet at fixed time intervals by means of a dissolution test "paddle" apparatus (U.S.P. XX, page 959). One tablet is placed in the vessel containing 500 ml of pH 1.2 buffer (simulated gastric fluid without enzymes, U.S.P. XX, page 1105) and kept under 125 RPM rotation at 37° C. during the test. At the first, fourth and eighth hours, samples are withdrawn and treated with hydrazine sulfate, sulfanilamid and N-(1-naphthyl)-ethylenediamine hydrochloride and the absorbence of the solution is determined at about 540 mm.

The following mixture was prepared and tableted as above.

| | | |
|---|---|---|
| Active ingredient Y | 80 | gm |
| HPMC E-50 | 20 | " |
| HPMC E-4M | 40 | " |
| HPMC K-15 | 10 | " |
| HPC | 10 | " |
| Stearic Acid | 1 | " |
| Syloid | 1 | " |

COMPARATIVE EXAMPLE V-A

The base ingredients listed in Example V were mixed for about 20 minutes in a Day powder mixer or a Pony mixer. Active ingredient was added to the base mixture and the mixture was again mixed for about 30 minutes adding lubricants. The mixture was then tableted immediately in a Stokes B2 Rotary machine or Manesty machine set to a compression of 9 kg/cm$^2$. The tablets were compressed into scored, capsule-shaped tablets. The punch size was 19.1 mm × 9.7 mm and the hardness was 9 kg/cm$^2$. In each instance, the potency of the tablet was 85 mg. Release of active ingredient was determined as described in Example V.

Comparison of Oral Tablets of The Invention With Tablets Oral of The Prior Art FIG. 5 shows curves of the release of active ingredient from the two sets of tablets of Example V, 26, prepared according to the invention and one set of tablets prepared according to prior art method (Example V-A) 28. It is clear that the unbonded tablet (Example V-A) reached the highest active level almost immediately and then the release suffered a sharp drop at the third hour. The active level from the tablet of comparative example V-A was substantially lower in the later hours of the test than from either of the tablets prepared according to the method of the invention.

EXAMPLE VI

Method of Tablet Preparation

The base ingredients listed below were mixed for about 20 minutes in a Day powder mixer or a Pony mixer. Active ingredient was added to the base mixture and the mixture was again mixed for about 30 minutes adding lubricants. Finally the complete mixture was permitted to temper for bonding for not less than 24 hours at room temperature. The mixture was then tableted in a Stokes B2 rotary machine or a Manesty machine set to a compression of 9 kg/cm$^2$. The tablets were compressed into scored capsule-shaped tablets. The punch size was 19.1 mm×9,7 mm and the hardness was 9 kg/cm$^2$. In each instance, the potency of the tablet was 104 mg.

The following formulation was prepared:

| | | |
|---|---|---|
| Active ingredient Z | 100 | gm |
| HPMC E-50 | 20 | " |
| HPMC E-4M | 40 | " |
| HPMC K-15 | 10 | " |
| HPC | 10 | " |
| Stearic Acid | 1 | " |

| | |
|---|---|
| -continued | |
| Syloid | 1 " |

Release of Active Ingredient

Figure 6:
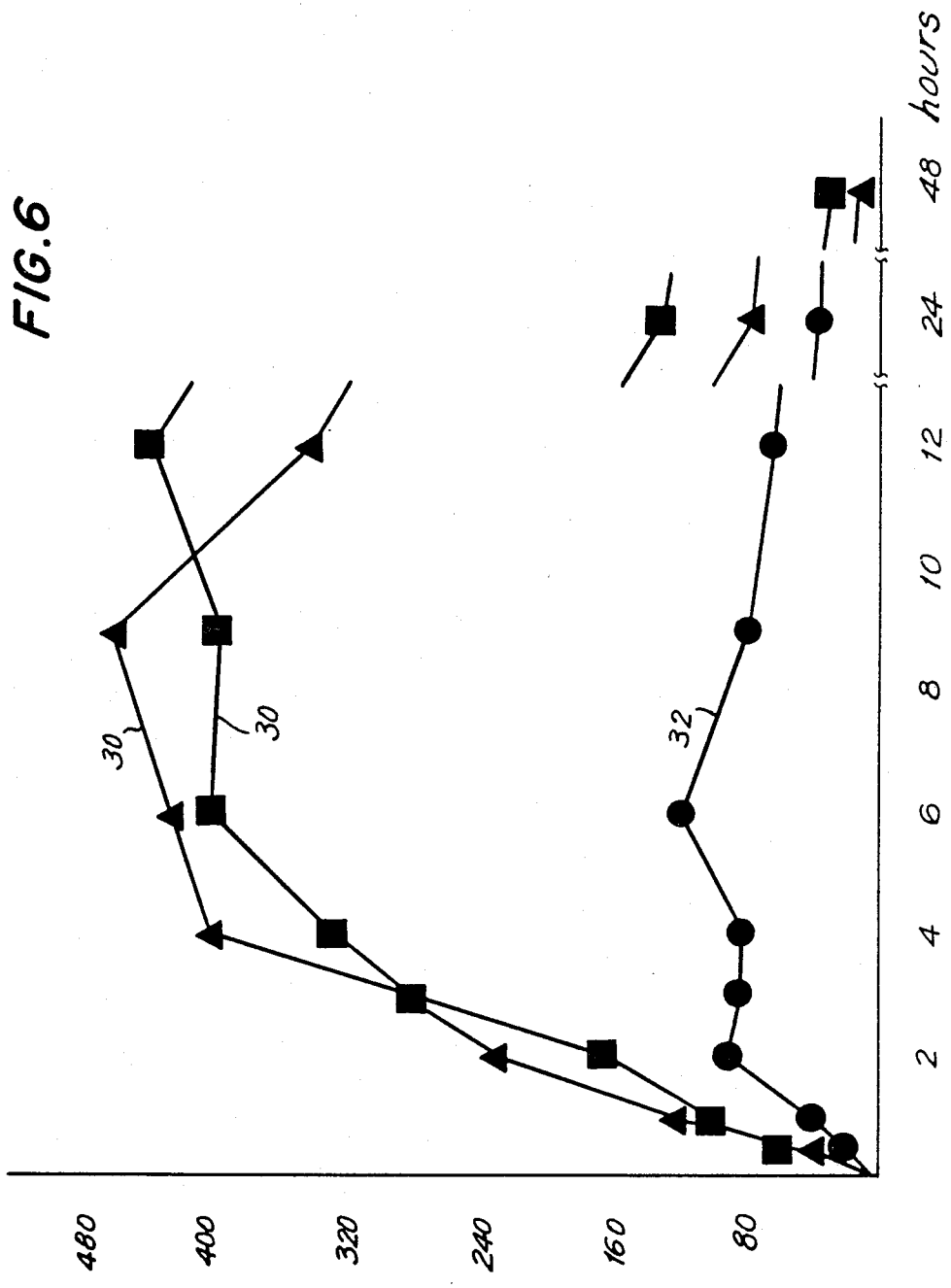

The release of active ingredient from the tablets prepared in Example VI was determined by blood level tests performed, in each instance, on six volunteers. The mean value of the blood level of active ingredient at the indicated time intervals is shown in FIG. 6. Venous blood samples were obtained from each subject just prior to and at 0.25, 0.5, 0.75, 1.00. 1.5, 2.0, 2.5, 3.0, 4.0, 6.0, 9.0, 12.0, 24.0, 36.0 and 48.0 hour times after dosing. In all six (6) subjects, arterial blood pressure was also measured just prior to dosing, and at 1.0, 2.0, 4.0, 6.0 and 9.0 hours after dosing.

The release of active ingredient over time can also be determined by an in vitro assay. This assay determines the percent of the drug released by a single tablet at fixed time intervals by means of a dissolution test "paddle" apparatus (U.S.P. XX, page 959). One tablet is placed in the vessel containing 500 ml of pH 1.2 buffer (simulated gastric fluid without enzymes, U.S.P. XX, page 1105) and kept under 125 RPM rotation at 37° C. during the test. At the first, fourth and eighth hours, samples are withdrawn and treated with hydrazine sulfate, sulfanilamid and N-(1-naphthyl)-ethylenediamine hydrochloride and the absorbence of the solution is determined at about 540 nm.

COMPARATIVE EXAMPLE VI-A

Method of Oral Tablet Preparation

The base ingredients listed in Example VI are mixed for about 20 minutes in a Day powder mixer or a Pony mixer. Active ingredient is added to the base mixture and the mixture is again mixed for about 30 minutes adding lubricants. The mixture is then immediately tableted in a Stokes B2 Rotary machine or Manesty machine set to a compression of 9 kg/cm$^2$. The tablets were compressed into scored, capsule-shaped tablets. The punch size was 19.1 mm×9.7 mm and the hardness was 9 kg/cm$^2$. In each instance, the potency of the tablet was 104 mg. Release of active ingredient was determined as in Example VI.

FIG. 6 describes the release of active ingredient from two sets of tablets of Example VI prepared according to the invention, 30, and a commercially available tablet of the prior art, 32. FIG. 6 shows that both tablets prepared according to the invention acted in a similar manner over a period of twelve hours.

EXAMPLE VII

On a different day, a control (comparison) batch of product Z was made with the same formula as Example VI and the finished tablets were tested again the same way as in Example VI for comparison of results. FIG. 7, reference numeral 34, demonstrates that the release of active ingredient from two bonded tablets was substantially the same as the release of active ingredient from the tablets prepared earlier as described in Example VI.

What is claimed is:

1. A multiplicity of uniform batches of unit doses of a controlled, long-acting release pharmaceutical formulation, in oral tablet form, wherein each of said doses contains active therapeutic agent and a carrier base material, and wherein each of said unit doses has uniform bioavailability from batch to batch, said unit doses being prepared by a method comprising the steps of:
   (a) adding a quantity of solid, particulate carrier base material consisting essentially of at least one cellulosic ether selected from the group consisting of hydroxypropyl methylcellulose, hydroxypropyl cellulose, carboxymethyl cellulose and ethyl cellulose, to a quantity of a therapeutically active pharmaceutical agent in granular or powder form;
   (b) mechanically mixing the carrier base material and the therapeutically active agent to form a uniform mixture;
   (c) discontinuing the mixing and permitting the mixture formed in step (a) to stand for a period of time from 2-27 hours to cause the therapeutically active pharmaceutical agent to become bonded to the carrier base material; and
   (d) compressing portions of the mixture formed in steps (b) and (c) into solid oral tablet doses, wherein release of said therapeutic agent from a unit dose of a given batch is substantially the same as release of said therapeutic agent from a unit dose of another batch.

2. A multiplicity of uniform batches of unit doses as recited in claim 1, wherein the mixture formed in step (b) is permitted to stand for at least 2 hours before compression into a unit dosage form.

3. A unit dosage form of a controlled, long-acting release pharmaceutical formulation wherein each of said unit dosages contains an active therapeutic agent and a carrier base material, and wherein each of said unit dosages has uniform bioavailability from batch to batch, said unit dosages being prepared by a method comprising the steps of:
   (a) thoroughly mixing a carrier base material comprising at least one cellulosic ether with a therapeutic agent to form a substantially uniform pharmaceutical formulation;
   (b) discontinuing the mixing step and permitting the mixture formed in step (a) to stand for a period of time sufficient to cause the said therapeutic agent to become bonded to the said cellulosic ether; and
   (c) compressing the said pharmaceutical formulation into a suitable unit dosage form wherein release, from batch to batch, is not faster, from one unit dosage to another.

4. A unit dosage form as recited in claim 3, wherein the carrier comprises one or more hydroxyalkyl cellulose or hydroxyalkyl alkylcellulose or derivatives thereof.

5. A unit dosage form as recited in claim 3, wherein the carrier comprises one or more of the cellulose ethers, hydroxypropyl methylcellulose, hydroxypropyl cellulose, carboxymethyl cellulose and ethylcellulose or derivatives thereof.

6. A unit dosage form as recited in claim 3 wherein the mixture formed in step (a) is permitted to stand for at least 2 hours before compression into a unit dosage form.

7. A unit dosage form, as recited in claim 3 wherein the active therapeutic agent is isosorbide mononitrate.

8. A unit dosage form, as recited in claim 3 wherein the active therapeutic agent is isosorbide dinitrate.

9. A unit dosage form, as recited in claim 3 wherein the active therapeutic agent is theophylline.

10. A unit dosage form, as recited in claim 3 wherein the active therapeutic agent is nitroglycerin.

11. A unit dosage form, as recited in claim 3 wherein the active therapeutic agent is ibuprofen.

12. A unit dosage form, as recited in claim 3 wherein the active therapeutic agent is acetaminophe.

* * * * *